United States Patent [19]
Shudy

[11] Patent Number: 5,491,736
[45] Date of Patent: Feb. 13, 1996

[54] HEAD POSITIONER FOR CAT SCANS

[76] Inventor: Glenn R. Shudy, W249 S7420 Center Dr., Waukasha, Wis. 53186

[21] Appl. No.: 374,968

[22] Filed: Jan. 19, 1995

[51] Int. Cl.$^6$ .............................. A47B 71/00; H05G 1/00
[52] U.S. Cl. ................. 378/20; 378/208; 5/601; 5/622
[58] Field of Search ...................... 378/195, 208, 378/209, 204, 20; 5/601, 622

[56] References Cited

U.S. PATENT DOCUMENTS

| | | | |
|---|---|---|---|
| 3,897,777 | 8/1975 | Morrison | 378/208 |
| 4,074,373 | 2/1978 | Garofalo | 5/601 |
| 4,616,814 | 10/1986 | Harwood-Nash et al. | 5/601 |
| 5,233,713 | 8/1993 | Murphy et al. | 5/601 |
| 5,370,117 | 12/1994 | McLaurin, Jr. | 378/208 |

*Primary Examiner*—David P. Porta
*Assistant Examiner*—Don Wong

[57] ABSTRACT

A head positioner for CAT scans comprised of a first receptacle. The device contains a slider having a threaded rod. The threaded rod has an open first end and second end. The open first end of the threaded rod extends outwardly of the slider. The slider is secured within the first receptacle with the open first end of the rod extending outwardly of the first receptacle. A second receptacle secures the slider to the first receptacle. A crank is securable to the open first end of the threaded rod of the slider.

3 Claims, 4 Drawing Sheets

HEAD POSITIONER FOR CAT SCANS

BACKGROUND OF THE INVENTION

1. Field of the Invention

The present invention relates to a head positioner for CAT scans and, more particularly, pertains to moving a patient's head left or right in order to place the head in the proper position for an x-ray with a head positioner for CAT scans.

2. Description of the Prior Art

The use of head positioners is known in the prior art. More specifically, head positioners heretofore devised and utilized for the purpose of adjusting the head for x-rays are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 5,311,882 to Gagne discloses a tomography head restraint.

U.S. Pat. No. 5,276,927 to Day discloses a radiolucent head support.

U.S. Pat. No. 5,263,494 to Margelos et al. discloses a head positioner for cephalometric x-ray.

U.S. Pat. No. 4,850,003 to Huebeck et al. discloses an apparatus for positioning a patient's head for producing remote x-ray photographs.

Lastly, U.S. Pat. No. 3,936,641 to Heimur discloses a head immobilizing device for panoramic x-ray apparatus.

While these devices fulfill their respective, particular objective and requirements, the aforementioned patents do not describe a head positioner for CAT scans for moving a patient's head left or right in order to place the head in the proper position for an x-ray.

In this respect, the head positioner for CAT scans according to the present invention substantially departs from the conventional concepts and designs of the prior art, and in so doing provides an apparatus primarily developed for the purpose of moving a patient's head left or right in order to place the head in the proper position for an x-ray with a head positioner for CAT scans.

Therefore, it can be appreciated that there exists a continuing need for a new and improved head positioner for CAT scans which can be used for moving a patient's head left or right in order to place the head in the proper position for an x-ray with a head positioner for CAT scans. In this regard, the present invention substantially fulfills this need.

SUMMARY OF THE INVENTION

In view of the foregoing disadvantages inherent in the known types of head positioners now present in the prior art, the present invention provides an improved head positioner for CAT scans. As such, the general purpose of the present invention, which will be described subsequently in greater detail, is to provide a new and improved head positioner for CAT scans and method which has all the advantages of the prior art and none of the disadvantages.

To attain this, the present invention essentially comprises a first receptacle having a first end, a second end, an inner surface, and an outer surface. The outer surface has two dowel pins extending outwardly therefrom. The two dowel pins secure the first receptacle to holes on an end of a table cradle. The inner surface has a plurality of apertures formed therein. The inner surface has a slot formed therein. The slot extends from the first end to the second end. The first end has a half moon-shaped opening corresponding with the slot. The second end has a half moon-shaped retaining slot formed therein corresponding with the slot. The device contains a slider having a first end, a second end, an intermediate extent therebetween, a first wall, and a second wall. A threaded aperture is formed through the first end and extends through the second end. The second wall has apertures formed therein inwardly of the first end and inwardly of the second end. The slider has a threaded rod. The threaded rod has an open first end and second end. The threaded rod is secured within the threaded aperture formed through the first end and extends through the second end. The open first end of the threaded rod extends outwardly of the first end of the slider and the second end of the threaded rod extends outwardly of the second end of the slider. The first wall of the slider is secured within the slot of the first receptacle with the open first end of the rod cooperating with the half moon-shaped opening in the first end of the first receptacle and the second end of the rod cooperating with the half moon-shaped retaining slot in the second end of the first receptacle. The device contains a second receptacle having a first end, a second end, an inner surface, and an outer surface. The inner surface has a slot formed therein. The slot extends from the first end to the second end. The first end has a half moon-shaped opening corresponding with the slot. The second end has a half moon-shaped retaining slot formed therein corresponding with the slot. The slot receives the second wall of the slider therein with the open first end of the rod cooperating with the half moon-shaped opening in the first end and the second end of the rod cooperating with the half moon-shaped retaining slot in the second end. The second receptacle has a plurality of apertures formed therethrough. The plurality of apertures align with the plurality of apertures in the inner surface of the first receptacle for securement thereto by screws. The outer surface has a pair of slots formed therethrough extending within the slot in the inner surface. The pair of slots align with the pair of apertures formed in the second wall. The pair of slots allow a pair of dowel pins of a head holder to couple with the pair of apertures in the second wall of the slider. A crank is securable to the open first end of the threaded rod of the slider.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved head positioner for CAT scans which has all the advantages of the prior art head positioners and none of the disadvantages.

It is another object of the present invention to provide a new and improved head positioner for CAT scans which may be easily and efficiently manufactured and marketed.

It is a further object of the present invention to provide a new and improved head positioner for CAT scans which is of a durable and reliable construction.

An even further object of the present invention is to provide a new and improved head positioner for CAT scans which is susceptible of a low cost of manufacture with regard to both materials and labor, and which accordingly is then susceptible of low prices of sale to the consuming public, thereby making such head positioners economically available to the buying public.

Still yet another object of the present invention is to provide a new and improved head positioner for CAT scans which provides in the apparatuses and methods of the prior art some of the advantages thereof, while simultaneously overcoming some of the disadvantages normally associated therewith.

Even still another object of the present invention is to provide a new and improved head positioner for CAT scans for moving a patient's head left or right in order to place the head in the proper position for an x-ray.

Lastly, it is an object of the present invention to provide a head positioner for CAT scans comprised of a first receptacle. The device contains a slider having a threaded rod. The threaded rod has an open first end and second end. The open first end of the threaded rod extends outwardly of the slider. The slider is secured within the first receptacle with the open first end of the rod extending outwardly of the first receptacle. A second receptacle secures the slider to the first receptacle. A crank is securable to the open first end of the threaded rod of the slider.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
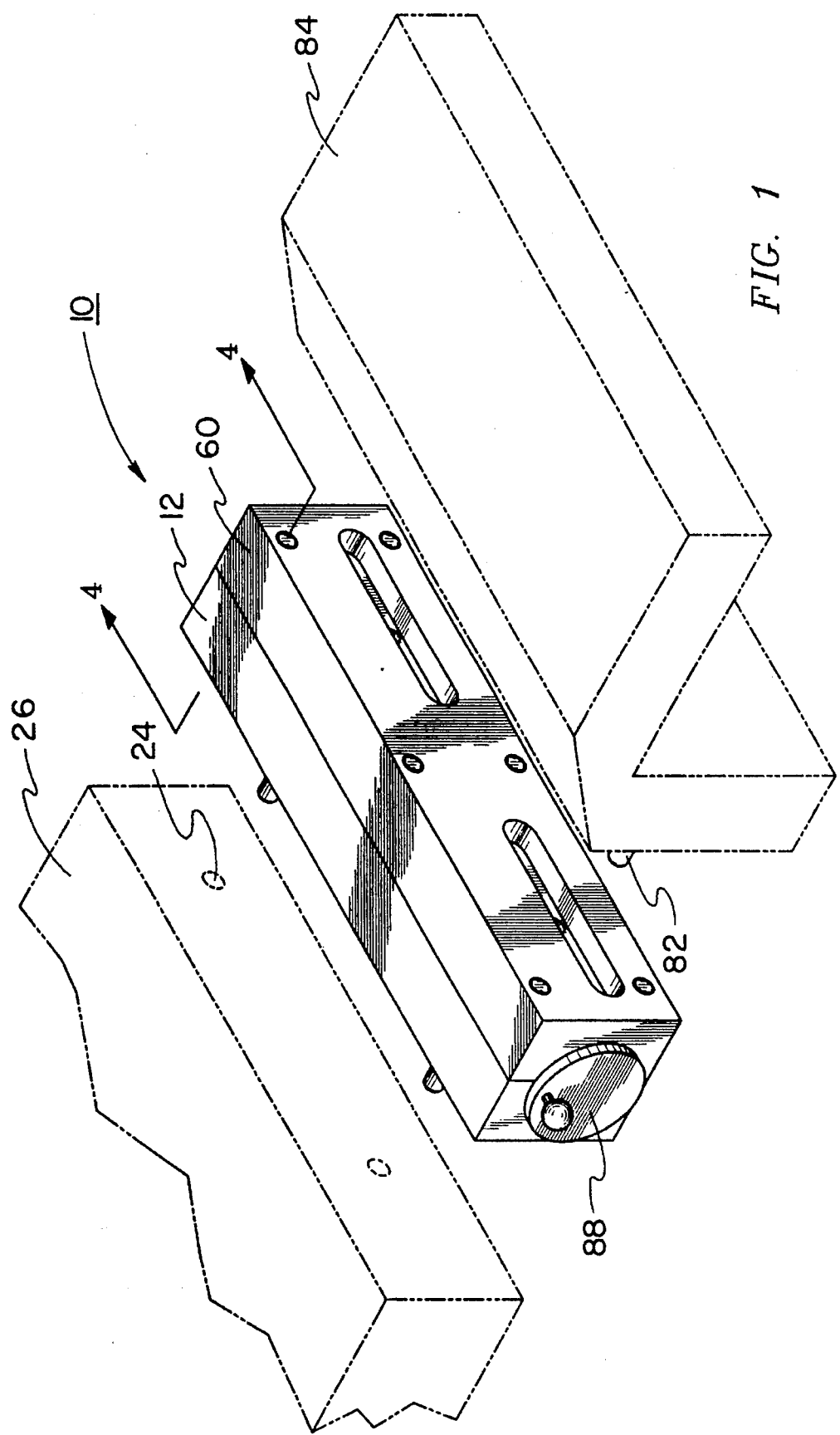
FIG. 1 is a perspective illustration of the preferred embodiment of the head positioner for CAT scans constructed in accordance with the principles of the present invention.
Figure 2:
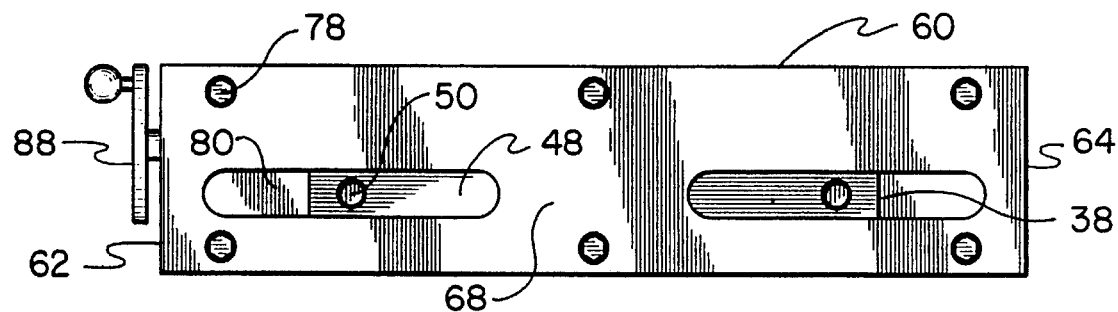
FIG. 2 is a side elevation view of the present invention.
Figure 3:
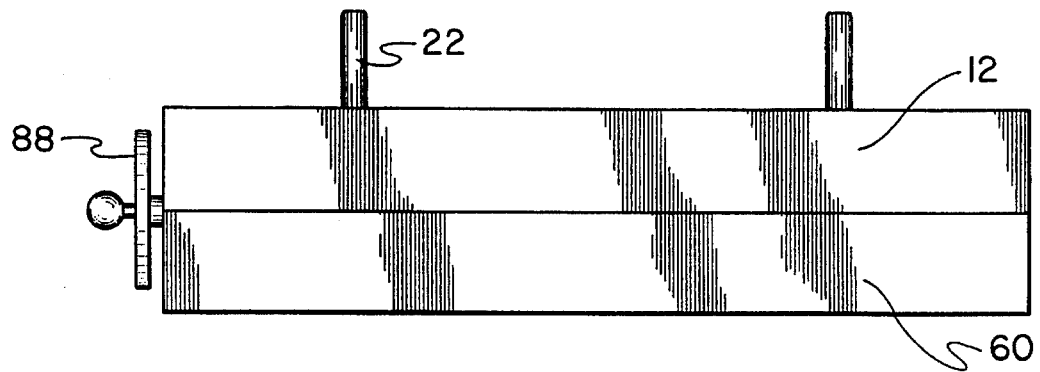
FIG. 3 is a plan view of the preferred embodiment of the present invention.
Figure 4:
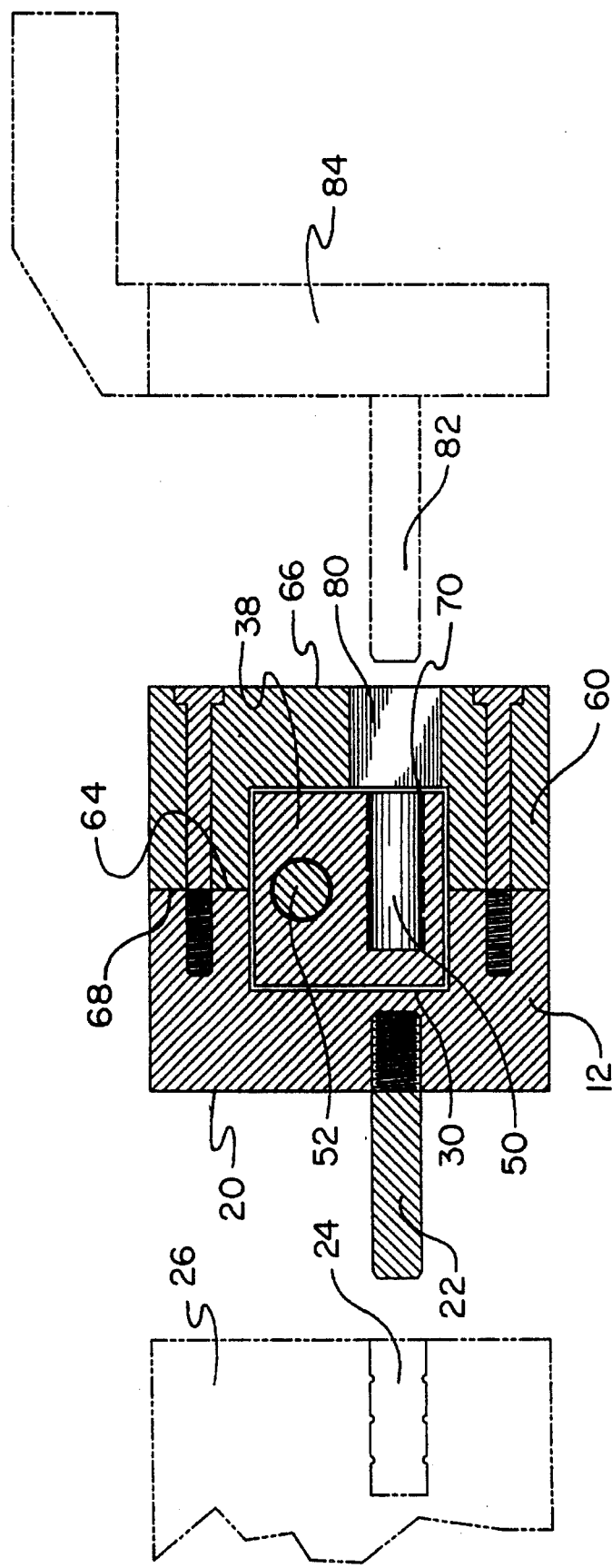
FIG. 4 is a cross-sectional view as taken along line 4—4 of FIG. 1.
Figure 5:
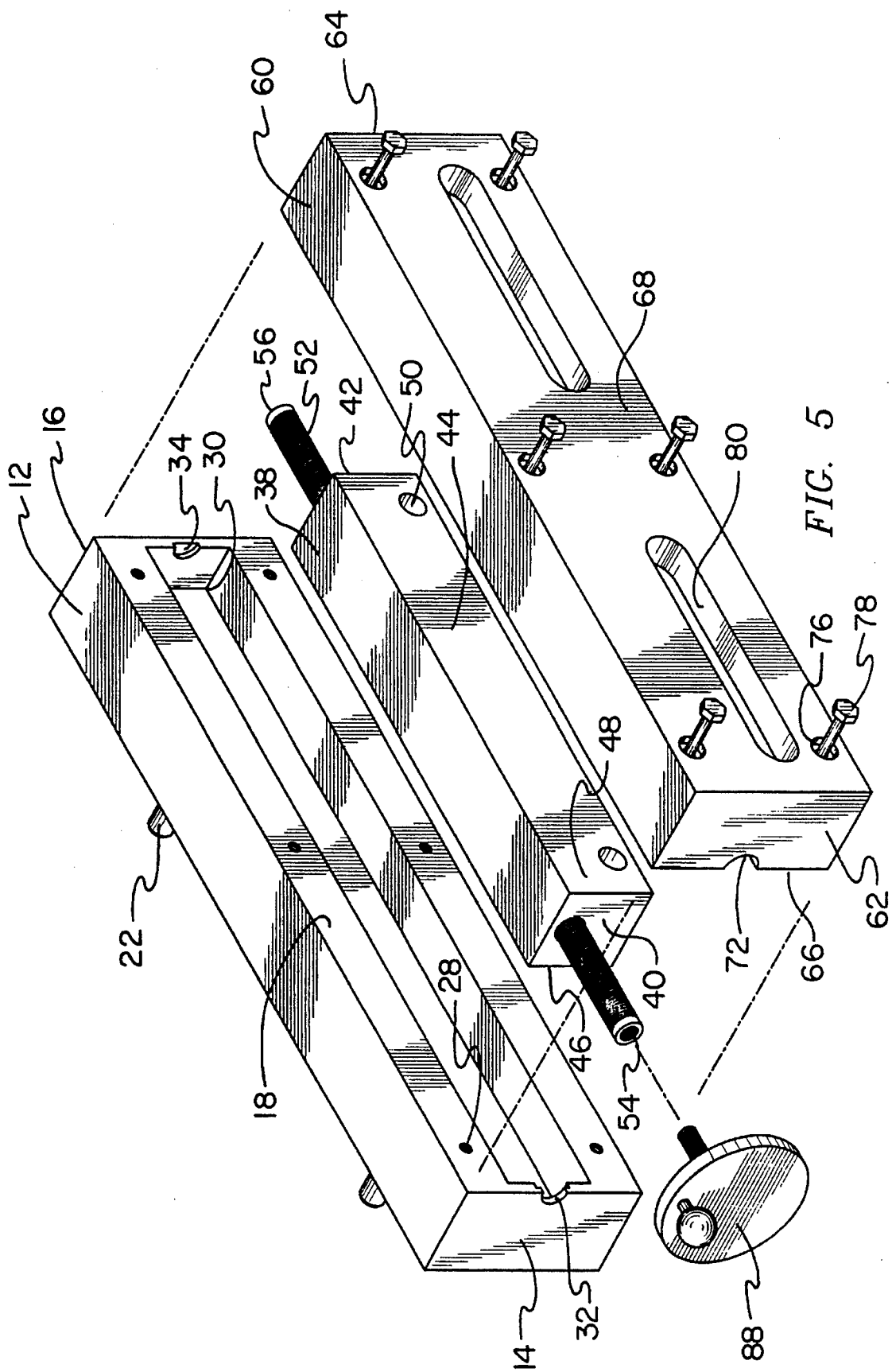
FIG. 5 is an exploded perspective view of the present invention. The same reference numerals refer to the same parts throughout the various Figures.

With reference now to the drawings, and in particular to FIG. 1 thereof, the preferred embodiment of the new and improved head positioner for CAT scans embodying the principles and concepts of the present invention and generally designated by the reference numeral 10 will be described.

Specifically, it will be noted in the various Figures that the device relates to a new and improved head positioner for CAT scans for moving a patient's head left or right in order to place the head in the proper position for an x-ray. In its broadest context, the device consists of a first receptacle, a slider, a second receptacle, and a crank.

The device 10 contains a first receptacle 12 having a first end 14, a second end 16, an inner surface 18, and an outer surface 20. The outer surface 20 has two dowel pins 22 extending outwardly therefrom. The two dowel pins 22 secure the first receptacle 12 to holes 24 on an end of a table cradle 26. The inner surface 18 has a plurality of apertures 28 formed therein. The inner surface 18 has a slot 30 formed therein. The slot 30 extends from the first end 14 to the second end 16. The first end 14 has a half moon-shaped opening 32 corresponding with the slot 30. The second end 16 has a half moon-shaped retaining slot 34 formed therein corresponding with the slot 30.

The device 10 contains a slider 38 having a first end 40, a second end 42, an intermediate extent 44 therebetween, a first wall 46, and a second wall 48. A threaded aperture is formed through the first end 40 and extends through the second end 42. The second wall 48 has a pair of apertures 50 formed therein inwardly of the first end 40 and inwardly of the second end 42. The slider 38 has a threaded rod 52. The threaded rod 52 has an open first end 54 and second end 56. The threaded rod 52 is secured within the threaded aperture formed through the first end 40 and extends through the second end 52. The open first end 54 of the threaded rod 52 extends outwardly of the first end 40 of the slider 38 and the second end 42 of the slider 38. The first wall 46 of the slider 38 is secured within the slot 30 of the first receptacle 12 with the open first end 54 of the rod cooperating with the half moon-shaped opening 32 in the first end 14 of the first receptacle 12 and the second end 56 of the rod 52 cooperating with the half moon-shaped retaining slot 34 in the second end 16 of the first receptacle 12.

The device 10 contains a second receptacle 60 having a first end 62, a second end 64, an inner surface 66, and an outer surface 68. The inner surface 64 has a slot 70 formed therein. The slot 70 extends from the first end 62 to the second end 64. The first end 62 has a half moon-shaped opening 72 corresponding with the slot 70. The second end 64 has a half moon-shaped retaining slot formed therein corresponding with the slot 70. The slot 70 receives the second wall 48 of the slider 38 therein with the open first end 54 of the rod 52 cooperating with the half moon-shaped opening 72 in the first end 62 and the second end 56 of the rod 52 cooperating with the half moon-shaped retaining slot in the second end 64. The second receptacle 60 has a plurality of apertures 76 formed therethrough. The plurality of apertures 76 align with the plurality of apertures 28 in the inner surface 18 of the first receptacle 12 for securement thereto by screws 78. The outer surface 68 has a pair of slots 80 formed therethrough extending within the slot 70 in the inner surface 66. The pair of slots 80 align with the pair of apertures 50 formed in the second wall 48 of the slider 38. The pair of slots 80 allow a pair of dowel pins 82 of a head holder 84 to couple with the pair of apertures 50 in the second wall 48 of the slider 38.

A crank 88 is securable to the open first end 54 of the threaded rod 52 of the slider 38. The crank 88 can be rotated to move the slider 38 along the threaded rod 52 to move the head holder 84 to the proper position in order to more effectively x-ray the patient's head.

This invention is a device 10 that moves the head holder 84 in a CAT scan x-ray machine left or right to place a patient's head in the proper location.

The device 10 consists of a hollow retainer 12,60 with a slider 38 inside it. All parts are machined out of aluminum. The retainer 12,60 has a pair of dowel pins 22 on one side that fit into the holes 24 on the end of the table cradle 26. A slot 80 on the opposite side provides access to a pair of holes 50 in the slider 38 into which the dowel pins 82 of the head holder 84 fit. A threaded rod 52 runs through the end plates on the retainer 12,60 and the slider 38 is threaded to accept the rod 52. The rod 52 has a crank handle 88 on one end and a collar on the other end to keep it in position. Turning the crank 88 moves the slider 38 inside the retainer 12,60. The retainer 12,60 uses two rectangular blocks, each with a large slot in one side, fastened together with the slots forming a rectangular channel in the center. The slider 38 is about two thirds as long as the retainer 12,60 and fits in the channel.

The device 10 plugs into the end of a table carrier and the head holder plugs into its dowel holes. When a patient's head is fastened into the head holder, the technician can turn the crank 88 to move the patient's head to the proper position.

The device 10 provides a faster and easier way to position a patient's head than with foam shims, and is much more accurate. It makes the technician more productive and allows more patients to be processed.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A head positioner for CAT scans for moving a patient's head left or right in order to place the head in the proper position for an x-ray comprising, in combination:

a first receptacle having a first end, a second end, an inner surface, and an outer surface, the outer surface having two dowel pins extending outwardly therefrom, the two dowel pins securing the first receptacle to holes on an end of a table cradle, the inner surface having a plurality of apertures formed therein, the inner surface having a slot formed therein, the slot extending from the first end to the second end, the first end having a half moon-shaped opening corresponding with the slot, the second end having a half moon-shaped retaining slot formed therein corresponding with the slot;

a slider having a first end, a second end, an intermediate extent therebetween, a first wall, and a second wall, a threaded aperture formed through the first end and extending through the second end, the second wall having apertures formed therein inwardly of the first end and inwardly of the second end, the slider having a threaded rod, the threaded rod having an open first end and second end, the threaded rod secured within the threaded aperture formed through the first end and extending through the second end, the open first end of the threaded rod extending outwardly of the first end of the slider and the second end of the threaded rod extending outwardly of the second end of the slider, the first wall of the slider secured within the slot of the first receptacle with the open first end of the rod cooperating with the half moon-shaped opening in the first end of the first receptacle and the second end of the rod cooperating with the half moon-shaped retaining slot in the second end of the first receptacle;

a second receptacle having a first end, a second end, an inner surface, and an outer surface, the inner surface having a slot formed therein, the slot extending from the first end to the second end, the first end having a half moon-shaped opening corresponding with the slot, the second end having a half moon-shaped retaining slot formed therein corresponding with the slot, the slot receiving the second wall of the slider therein with the open first end of the rod cooperating with the half moon-shaped opening in the first end and the second end of the rod cooperating with the half moon-shaped retaining slot in the second end, the second receptacle having a plurality of apertures formed therethrough, the plurality of apertures aligning with the plurality of apertures in the inner surface of the first receptacle for securement thereto by screws, the outer surface having a pair of slots formed therethrough extending within the slot in the inner surface, the pair of slots aligning with the pair of apertures formed in the second wall, the pair of slots allowing a pair of dowel pins of a head holder to couple with the pair of apertures in the second wall of the slider;

a crank securable to the open first end of the threaded rod of the slider.

2. A head positioner for CAT scans for moving a patient's head left or right in order to place the head in the proper position for an x-ray comprising:

a first receptacle;

a slider having a threaded rod, the threaded rod having an open first end and second end, the open first end of the threaded rod extending outwardly of the slider, the slider secured within the first receptacle with the open first end of the rod extending outwardly of the first receptacle;

a second receptacle securing the slider to the first receptacle; and a crank securable to the open first end of the threaded rod of the slider.

3. The head positioner as described in claim 1 and further including wherein the first receptacle, the slider, the second receptacle and the crank are machined out of aluminum.

\* \* \* \* \*